US012336691B2

(12) United States Patent
Wakabayashi et al.

(10) Patent No.: US 12,336,691 B2
(45) Date of Patent: Jun. 24, 2025

(54) DISTAL END PORTION OF ENDOSCOPE, DISTAL END FRAME, ENDOSCOPE, AND ELECTRIC CONDUCTION CONFIRMATION METHOD

(71) Applicant: OLYMPUS CORPORATION, Tokyo (JP)

(72) Inventors: Toru Wakabayashi, Hachioji (JP); Junya Yamada, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 387 days.

(21) Appl. No.: 17/898,884

(22) Filed: Aug. 30, 2022

(65) Prior Publication Data

US 2022/0409032 A1    Dec. 29, 2022

Related U.S. Application Data

(63) Continuation of application No. PCT/JP2020/009882, filed on Mar. 6, 2020.

(51) Int. Cl.
*A61B 1/00* (2006.01)
*A61B 1/018* (2006.01)
(Continued)

(52) U.S. Cl.
CPC .......... *A61B 1/051* (2013.01); *A61B 1/00057* (2013.01); *A61B 1/00096* (2013.01); *A61B 1/018* (2013.01); *A61B 1/04* (2013.01)

(58) Field of Classification Search
CPC . A61B 1/051; A61B 1/00057; A61B 1/00096; A61B 1/018; A61B 1/04; A61B 1/05; A61B 1/00027; A61B 18/16
(Continued)

(56) References Cited

U.S. PATENT DOCUMENTS 4,832,003 A * 5/1989 Yabe ...................... A61B 1/051
600/109
7,842,046 B1 * 11/2010 Nakao ................ A61B 17/0469
606/144
(Continued)

FOREIGN PATENT DOCUMENTS

| JP | 2017-209278 A | 11/2017 |
| JP | 2020-010744 A | 1/2020 |
| WO | 2016/203830 A1 | 12/2016 |

OTHER PUBLICATIONS

International Search Report dated May 26, 2020 received in PCT/JP2020/009882.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

A distal end portion includes: an imager that is held by a metal lens frame; a distal end frame that is made of an electric insulating material and includes a through hole; an electrically conductive exterior portion; a first electrical conductor pattern that has a first end and a second end, the first end being in contact with the lens frame, the second end being connected to a first terminal that is in contact with the exterior portion; and a second electrical conductor pattern that is formed independently of the first electrical conductor pattern, and has a first end and a second end, the first end of the second electrical conductor pattern being in contact with the lens frame, the second end of the second electrical conductor pattern being connected to a second terminal that is not in contact with the exterior portion.

20 Claims, 9 Drawing Sheets

(51) Int. Cl.
*A61B 1/04* (2006.01)
*A61B 1/05* (2006.01)

(58) Field of Classification Search
USPC .......................................................... 600/104
See application file for complete search history.

(56) References Cited

U.S. PATENT DOCUMENTS

| | | | |
|---|---|---|---|
| 2010/0231702 A1* | 9/2010 | Tsujimura .......... | A61B 1/00124 348/E7.091 |
| 2017/0265715 A1 | 9/2017 | Nishina et al. | |
| 2020/0015664 A1 | 1/2020 | Hatase et al. | |

* cited by examiner

DISTAL END PORTION OF ENDOSCOPE, DISTAL END FRAME, ENDOSCOPE, AND ELECTRIC CONDUCTION CONFIRMATION METHOD

CROSS-REFERENCE TO RELATED APPLICATION

This application is a continuation of International Application No. PCT/JP2020/009882, filed on Mar. 6, 2020, the entire contents of which are incorporated herein by reference.

BACKGROUND

1. Technical Field

The present disclosure relates to a distal end portion of an endoscope inserted into a subject, a distal end frame, an endoscope, and an electric conduction confirmation method.

2. Related Art

In the related art, an endoscope inserts a flexible insertion portion having an elongated shape, in which an imager is provided at a distal end, into a subject such as a patient, acquires image data in the subject by the imager disposed at a distal end portion, and transmits the image data to an external information processing apparatus by a signal cable.

In recent years, there has been proposed an endoscope in which a distal end frame of an insertion portion is switched from metal to resin, but in order to use a member made of resin, a mechanism for preventing destruction of an image sensor, in a case where static electricity is applied, is required.

As a technique for preventing a leakage current and static electricity from flowing through the image sensor, an endoscope has been proposed in which a circuit pattern is provided on an inner peripheral surface of a fixing hole to which a lens frame of a distal end frame is fixed, and the endoscope is connected to a bendable tube that is an electrically conductive material (see, for example, JP 2017-209278 A).

SUMMARY

In some embodiments, provided is a distal end portion of an endoscope. The distal end portion includes: an imager that is held by a metal lens frame and includes an objective optical system and an image sensor; a distal end frame that is made of an electric insulating material and includes a through hole through which the imager is inserted; an electrically conductive exterior portion that has a distal end side connected to a proximal end side of the distal end frame and a proximal end side connected to a ground of an external device; a first electrical conductor pattern that has a first end and a second end, the first end of the first electrical conductor pattern being formed in the through hole and being in contact with the lens frame, the second end of the first electrical conductor pattern being connected to a first terminal that is formed on a proximal end side of an outer peripheral portion of the distal end frame and that is in contact with the exterior portion; and a second electrical conductor pattern that is formed independently of the first electrical conductor pattern, and has a first end and a second end, the first end of the second electrical conductor pattern being formed in the through hole and being in contact with the lens frame, the second end of the second electrical conductor pattern being connected to a second terminal that is formed outside the through hole of the distal end frame and that is not in contact with the exterior portion. The second terminal is configured to be directly or indirectly conducted electricity when the imager and the exterior portion are attached to the distal end frame.

In some embodiments, provided is a distal end frame that is made of an electric insulating material and that is used for a distal end portion of an endoscope. The distal end frame includes: a through hole through which an imager is inserted; a first electrical conductor pattern that has a first end and a second end, the first end of the first electrical conductor pattern being formed in the through hole and being in contact with a metal lens frame of the imager, the second end of the first electrical conductor pattern being connected to a first terminal formed on a proximal end side of an outer peripheral portion of the distal end frame; and a second electrical conductor pattern that is formed independently of the first electrical conductor pattern, and has a first end and a second end, the first end of the second electrical conductor pattern being formed in the through hole and being in contact with the lens frame, the second end of the second electrical conductor pattern being connected to a second terminal.

In some embodiments, an endoscope includes: a distal end portion that includes an imager that is held by a metal lens frame and includes an objective optical system and an image sensor, a distal end frame that is made of an electric insulating material and includes a through hole through which the imager is inserted, an electrically conductive exterior portion that has a distal end side connected to a proximal end side of the distal end frame and a proximal end side connected to a ground of an external device, a first electrical conductor pattern that has a first end and a second end, the first end of the first electrical conductor pattern being formed in the through hole and being in contact with the lens frame of the imager, the second end of the first electrical conductor pattern being connected to a first terminal that is formed on a proximal end side of an outer peripheral portion of the distal end frame and that is in contact with the exterior portion, and a second electrical conductor pattern that is formed independently of the first electrical conductor pattern, and has a first end and a second end, the first end of the second electrical conductor pattern being formed in the through hole and being in contact with the lens frame, the second end of the second electrical conductor pattern being connected to a second terminal that is formed outside the through hole of the distal end frame and that is not in contact with the exterior portion. The second terminal is configured to be directly or indirectly conducted electricity when the imager and the exterior portion are attached to the distal end frame.

In some embodiments, an electric conduction confirmation method includes: in an electric insulating distal end frame of an endoscope, the distal end frame including a through hole through which an imager is inserted, a protrusion that includes a second terminal and protrudes from a distal end surface or a proximal end surface of the distal end frame, a first electrical conductor pattern that has a first end and a second end, the first end of the first electrical conductor pattern being formed in the through hole and being in contact with a metal lens frame of the imager, the second end of the first electrical conductor pattern being connected to a first terminal formed on a proximal end side of an outer peripheral portion of the distal end frame, and a second electrical conductor pattern that is formed independently of the first electrical conductor pattern, and has a first end and a second end, the first end of the second electrical conductor pattern being formed in the through hole and in contact with the lens frame, the second end of the second electrical conductor pattern being connected to a second terminal of the protrusion, connecting an electrode of a tester to the second terminal to establish electric conduction between the first terminal and the second terminal; and confirming whether electric conduction is established between the first terminal and the second terminal.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following description, an endoscope system including a distal end portion of an endoscope will be described as an embodiment for carrying out the disclosure (hereinafter, referred to as "embodiment"). The disclosure is not limited to the following embodiments. Moreover, in the description of the drawings, the same parts are denoted by the same reference numerals. Furthermore, it should be noted that the drawings are schematic, and the relationship between the thickness and width of each member or portion, the ratio of each member or portion, and the like are different from the reality. In addition, parts of the drawings having different dimensions and ratios are included. The same components are denoted by the same reference numerals throughout the description of the embodiments.

First Embodiment

Figure 1:
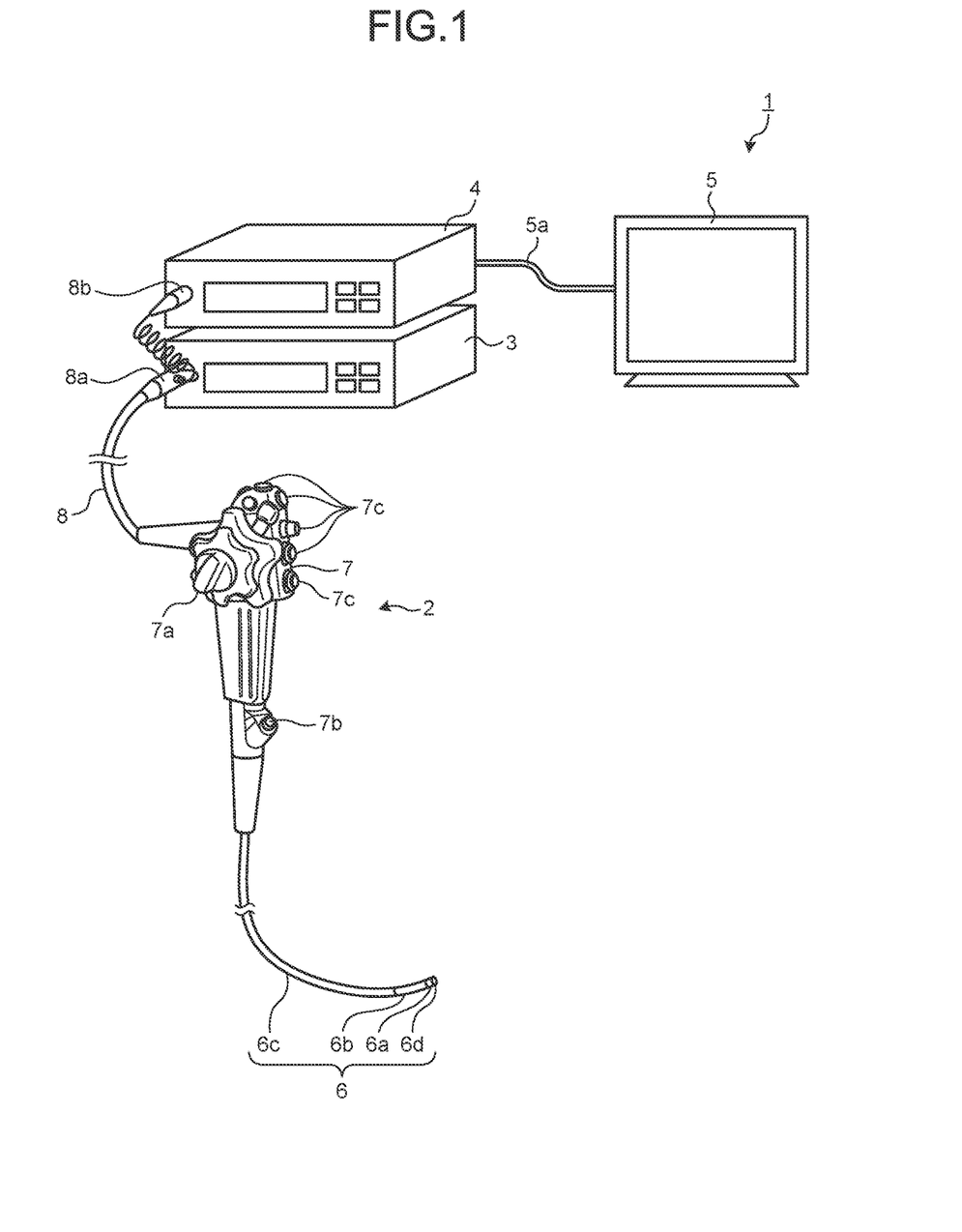
FIG. 1 is a schematic view schematically illustrating an overall configuration of an endoscope system according to a first embodiment of the disclosure.

FIG. 1 is a schematic view schematically illustrating an overall configuration of an endoscope system 1 according to a first embodiment of the disclosure. As illustrated in FIG. 1, an endoscope system 1 according to the first embodiment includes an endoscope 2 that is introduced into a subject and captures an image of the inside of the subject to generate an image signal of the inside of the subject, an information processing apparatus 3 that performs predetermined image processing on the image signal captured by the endoscope 2 and controls each unit of the endoscope system 1, a light source apparatus 4 that generates illumination light of the endoscope 2, and a display device 5 that displays an image of the image signal after the image processing by the information processing apparatus 3.

The endoscope 2 includes an insertion portion 6 to be inserted into a subject, an operating unit 7 which is a proximal end portion side of the insertion portion 6 and is gripped by an operator, and a flexible universal cord 8 extending from the operating unit 7.

The insertion portion 6 is realized by using a light guide cable, an electric cable, an optical fiber, and the like. The insertion portion 6 includes a distal end portion 6a incorporating an imager to be described later, a bending portion 6b that includes a plurality of pieces and is bendable, and a flexible tube portion 6c having flexibility provided on a proximal end portion side of the bending portion 6b. The distal end portion 6a is provided with a light guide cable that illuminates the inside of the subject, an imager that captures an image of the inside of the subject, and an aperture portion that communicates with a treatment tool channel.

The operating unit 7 includes a knob 7a that causes the bending portion 6b to bend in the vertical direction and the horizontal direction, a treatment tool insertion portion 7b through which a treatment tool such as a biological forceps or a laser scalpel is inserted into the body cavity of the subject, and a plurality of switch units 7c that operate peripheral apparatuses such as the information processing apparatus 3, the light source apparatus 4, an air supply apparatus, a water supply apparatus, and a gas supply apparatus. The treatment tool inserted from the treatment tool insertion portion 7b passes through a treatment tool channel provided inside and comes out from the aperture portion at the distal end of the insertion portion 6.

The universal cord 8 is configured using a light guide cable, an electric cable, or the like. The universal cord 8 is branched at a proximal end, and one branched end portion is a connector 8a and the other proximal end is a connector 8b. The connector 8a is detachable from the connector of the information processing apparatus 3. The connector 8b is detachable from the light source apparatus 4. The universal cord 8 propagates the illumination light emitted from the light source apparatus 4 to the distal end portion 6a via the connector 8b and the light guide cable. In addition, the universal cord 8 transmits an image signal captured by the imager to be described later to the information processing apparatus 3 via the cable and the connector 8a.

The information processing apparatus 3 performs predetermined image processing on the image signal output from the connector 8a and controls the entire endoscope system 1.

The light source apparatus 4 is configured using a light source that emits light, a condenser lens, and the like. Under the control of the information processing apparatus 3, the light source apparatus 4 emits light from the light source and supplies the light as illumination light for the inside of the subject as a subject to the endoscope 2 connected via the connector 8b and the light guide cable of the universal cord 8.

The display device 5 is configured using a display or the like using liquid crystal or organic electro luminescence (EL). The display device 5 displays various types of information including an image subjected to predetermined image processing by the information processing apparatus 3 via a video cable 5a. As a result, the operator can observe a desired position in the subject and determine the property by operating the endoscope 2 while viewing the image (in-vivo image) displayed by the display device 5.

Figure 2:
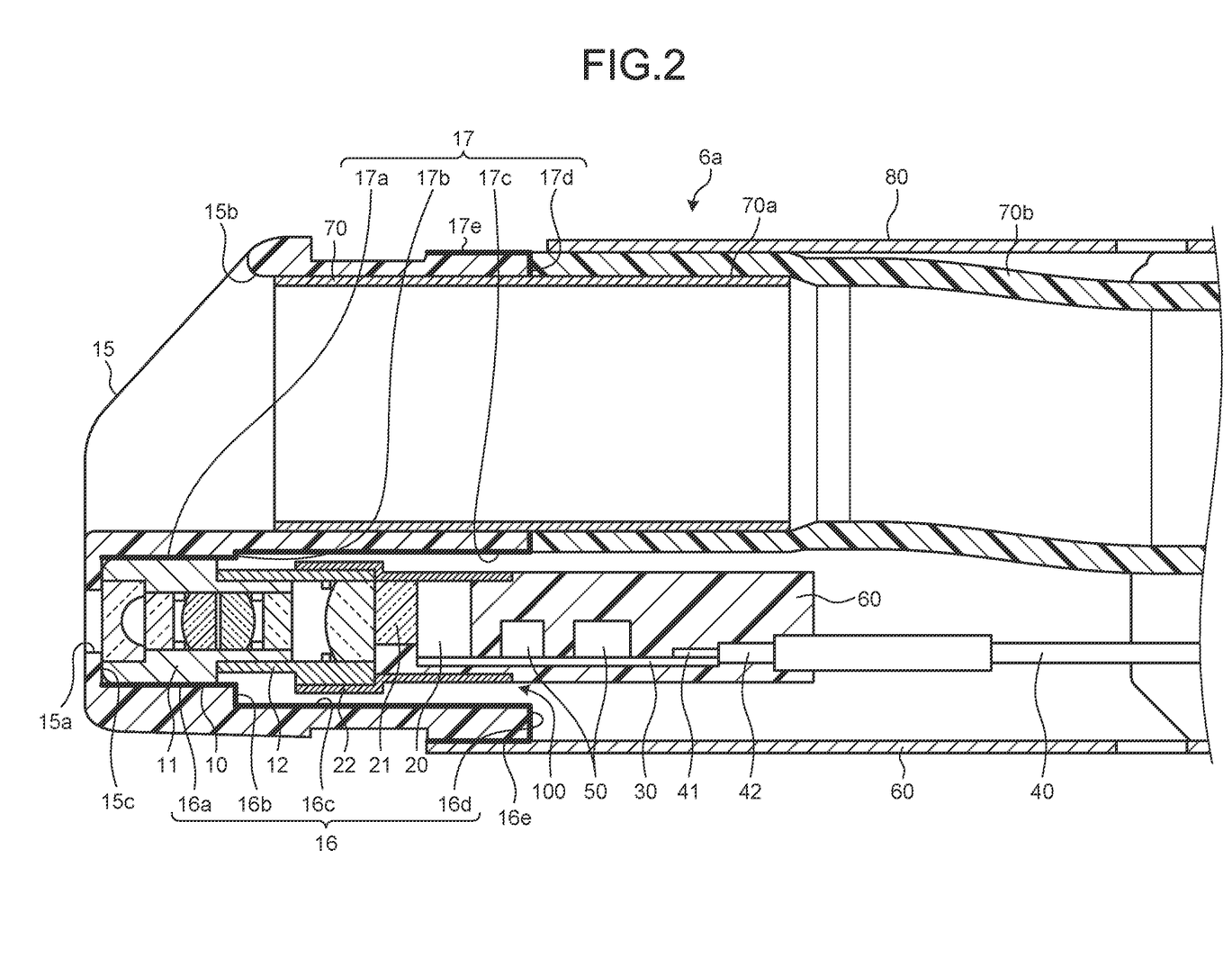
FIG. 2 is a cross-sectional view of a distal end portion of the endoscope illustrated in FIG. 1.
Figure 3:
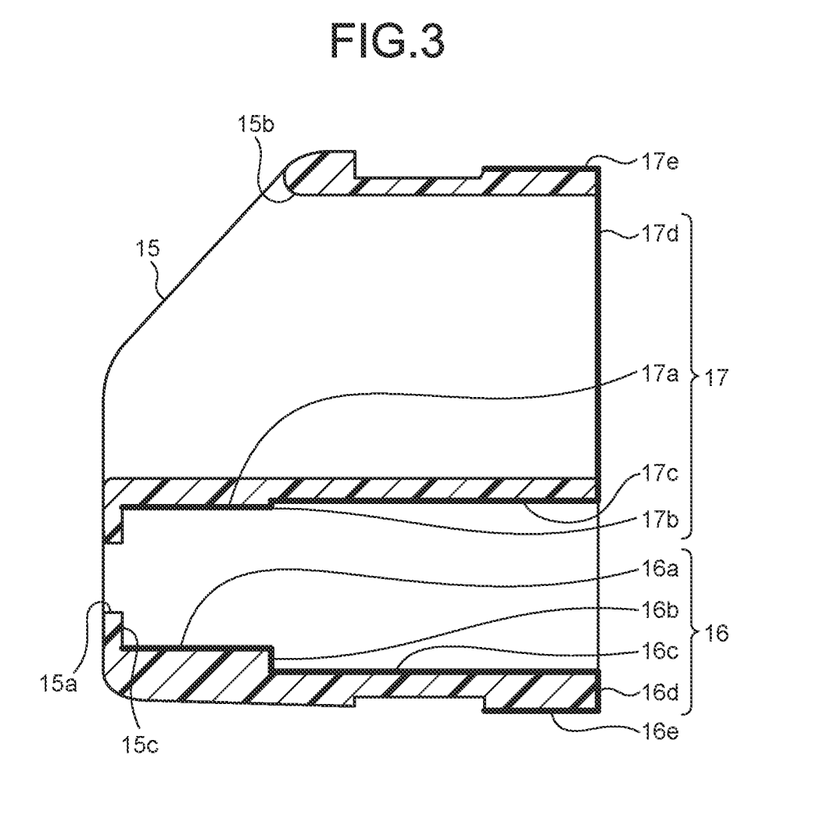
FIG. 3 is a cross-sectional view of a distal end frame used in the distal end portion illustrated in FIG. 2.

Next, the distal end portion 6a used in the endoscope system 1 will be described in detail. FIG. 2 is a cross-sectional view of the distal end portion 6a of the endoscope 2 illustrated in FIG. 1, and FIG. 3 is a cross-sectional view of a distal end frame 15 used in the distal end portion 6a illustrated in FIG. 2. In FIG. 2, illustration of an external coating is omitted. In the present specification, the distal end portion 6a side of the endoscope 2 is referred to as a distal end side, and the side from which a signal cable 40 extends is referred to as a proximal end side.

The distal end portion 6a of the endoscope 2 includes an imager 100 that captures a subject image, a treatment tool channel 70 through which a treatment tool is inserted, the distal end frame 15 having a through hole 15a through which the imager 100 is inserted and a channel through hole 15b through which the treatment tool channel 70 is inserted, and a bendable tube 80 that can bend the distal end portion 6a vertically or vertically and horizontally.

The imager 100 includes an objective optical system 10 that forms an image of a subject, an image sensor 20 that photoelectrically converts the subject image formed by the objective optical system 10 and generates an image signal, a circuit board 30, and the signal cable 40.

The objective optical system 10 includes a plurality of lenses from the distal end side toward the proximal end side along the optical axis. The plurality of lenses is held by a cylindrical first lens frame 11 made of metal. The first lens frame 11 is fixed to the distal end side of the through hole 15a of the distal end frame 15 with an adhesive.

The lens on the proximal end side among the plurality of lenses is held by a cylindrical second lens frame 12 made of metal. The distal end side of the second lens frame is externally fitted to the proximal end side of the first lens frame 11, and fixed with an electrically conductive adhesive.

A glass cover 21 for protecting a light receiver is bonded and fixed to the image sensor 20, and a surface of the glass cover 21 on the opposite side of the bonding surface with the image sensor 20 is fixed to the lens on the most proximal end side with an adhesive. The periphery of the image sensor 20 is covered with a metal reinforcing frame 22, and the distal end side of the reinforcing frame 22 is externally fitted to the proximal end side of the second lens frame 12 and fixed with an electrically conductive adhesive.

The image sensor 20 is mounted on the distal end side of the circuit board 30, and electronic components 50 such as a transistor and a capacitor are mounted on the circuit board 30. In addition, the signal cable 40 that transmits power and various signals to the image sensor or transmits an image signal from the image sensor is connected to the proximal end side of the circuit board 30. In the signal cable 40, an electric insulating jacket 42 on the distal end side is removed to expose a core wire 41, and the exposed core wire 41 is connected to the circuit board 30 by an electrically conductive material such as solder (not illustrated).

The inside of the reinforcing frame 22 (the periphery of the image sensor 20), the mounting regions of the electronic components 50 of the circuit board 30, and the periphery of the connection region of the signal cable 40 are sealed with a sealing resin 60.

The treatment tool channel 70 includes a frame portion 70a made of metal and a tube 70b made of resin externally fitted to the proximal end side of the frame portion 70a. The tube 70b has flexibility and is fixed to the frame portion 70a with an adhesive. The frame portion 70a is fixed to the channel through hole 15b of the distal end frame 15 with an adhesive.

The distal end portion of the bendable tube 80 is attached to the outer periphery on the proximal end side of the distal end frame 15. The bendable tube 80 is a bending piece set in which a plurality of pieces made of an electrically conductive material are rotatably connected by rivets. The pieces rotate around the rivets as wires arranged vertically and horizontally are pulled and relaxed by operation of the knob 7a, and the bending portion 6b is operated vertically or horizontally. In the present embodiment, the bendable tube 80 functions as an electrically conductive exterior portion. An electric insulating outer tube (not illustrated) is provided around the bendable tube 80.

Figure 4:
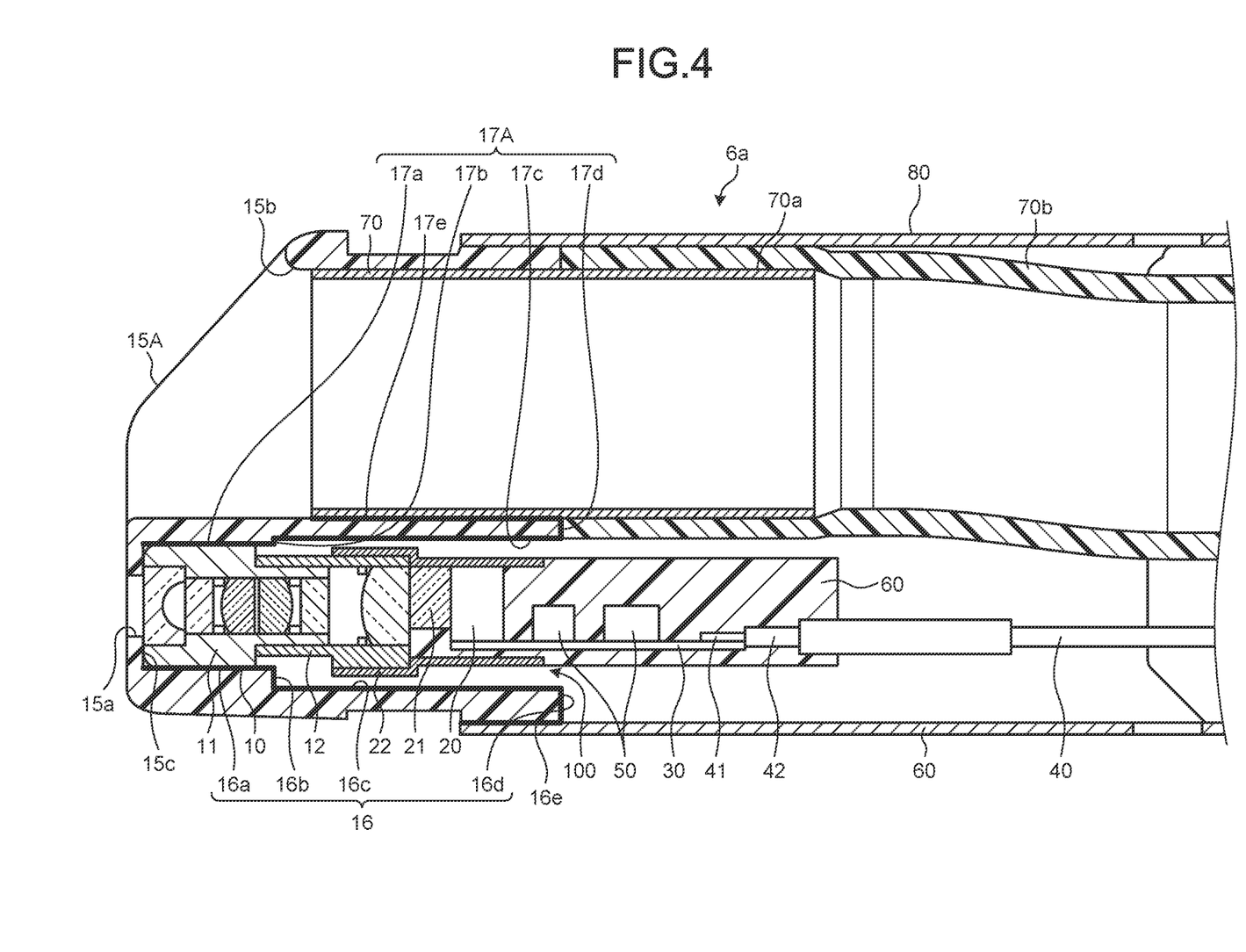
FIG. 4 is a cross-sectional view of a distal end portion of the endoscope according to a second embodiment.

The distal end frame 15 is made of an electric insulating material. As illustrated in FIGS. 3 and 4, the distal end frame 15 includes a first electrical conductor pattern 16 having one end that is formed in the through hole 15a through which the imager 100 is inserted and is in contact with the first lens frame 11, and another end that is connected to a first terminal 16e formed on the proximal end side of the outer peripheral portion of the distal end frame 15 and is in contact with the bendable tube 80, which is an exterior portion, and a second electrical conductor pattern 17 formed independently of the first electrical conductor pattern 16, having one end that is formed in the through hole 15a and is in contact with the first lens frame 11, and another end that is connected to a second terminal 17e formed on the proximal end side of the outer periphery of the distal end frame 15. The second terminal 17e is disposed on an outer periphery of the distal end frame 15 and on a side substantially opposite to a side on which the first terminal 16e is disposed. The distal end side of the bendable tube 80 is connected to the proximal end side of the distal end frame 15 and covers the periphery of the second terminal 17e similarly to the first terminal 16e, but in the first embodiment, a portion in contact with the second terminal 17e is cut out.

The first electrical conductor pattern 16 includes a first pattern 16a to which the imager 100 is fitted and which abuts on the first lens frame 11, a second pattern 16b provided at a step portion, a third pattern 16c provided on the proximal end side of the through hole 15a, and a fourth pattern 16d provided on the proximal end surface of the distal end frame 15, and the fourth pattern 16d is connected to the first terminal 16e.

The second electrical conductor pattern 17 includes a fifth pattern 17a to which the imager 100 is fitted and which abuts on the first lens frame 11, a sixth pattern 17b provided at a step portion, a seventh pattern 17c provided on the proximal end side of the through hole 15a, and an eighth pattern 17d provided on the proximal end surface of the distal end frame 15, and the eighth pattern 17d is connected to the second terminal 17e.

As illustrated in FIG. 2, the imager 100 is inserted into the through hole 15a, and the electrically conductive first lens frame 11 abuts on the first pattern 16a and the fifth pattern 17a.

In the distal end portion 6a of the endoscope 2, when static electricity or a leakage current is applied to the distal end frame 15 made of a resin having no electric conductivity, it is possible to conduct electricity from the first lens frame 11 to the ground of the operating unit 7 or the like through the first electrical conductor pattern 16 formed in the distal end frame 15, that is, the first pattern 16a, the second pattern 16b, the third pattern 16c, and the fourth pattern 16d by an exterior portion such as the first terminal 16e and the bendable tube 80, and it is possible to prevent destruction of the image sensor 20.

In the conventional distal end frame, in a state where the imager and the bendable tube are assembled in the distal end frame, the bendable tube covers the entire proximal end side of the distal end frame, so that electric conduction of the discharge path cannot be confirmed. In addition, although not illustrated in JP 2017-209278 A, since an abutting portion 15c that abuts on and positions the imager 100 is provided on the distal end side of the through hole 15a, it is not possible to conduct electricity from the distal end side of the through hole 15a to the first lens frame 11. On the other hand, in the first embodiment, the second electrical conductor pattern 17, which includes the fifth pattern 17a, the sixth pattern 17b, the seventh pattern 17c, and the eighth pattern 17d and is connected to the second terminal 17e, is provided, for confirming a discharge path, independently of the first electrical conductor pattern 16 that performs discharge, and the bendable tube 80 on the second terminal 17e is cut out. As a result, an electrode of a tester for performing electric conductivity confirmation can be directly connected to the second terminal 17e and the bendable tube that performs discharge, and it is possible to easily confirm whether the first electrical conductor pattern 16 and the second electrical conductor pattern 17 are electrically connected via the second terminal 17e.

Second Embodiment

Figure 5:
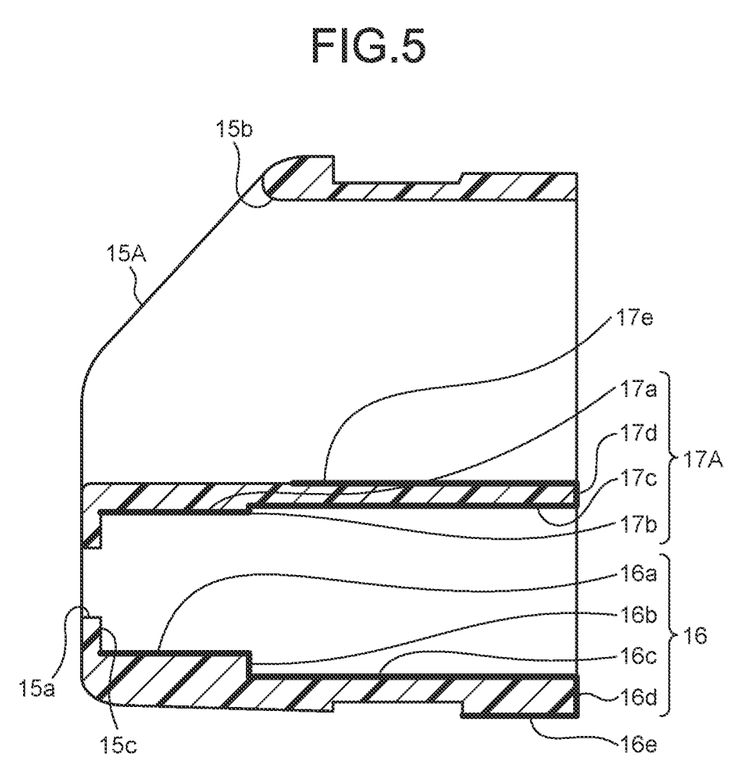
FIG. 5 is a perspective view of a distal end frame used in the distal end portion illustrated in FIG. 4.

In a second embodiment, the second terminal 17e is formed in the channel through hole 15b. FIG. 4 is a cross-sectional view of the distal end portion 6a of the endoscope 2 according to the second embodiment, and FIG. 5 is a cross-sectional view of a distal end frame 15A used in the distal end portion 6a illustrated in FIG. 4. In FIG. 4, illustration of an external coating is omitted.

The distal end frame 15A includes the first electrical conductor pattern 16 having one end that is formed in the through hole 15a through which the imager 100 is inserted and is in contact with the first lens frame 11, and another end that is connected to the first terminal 16e formed on the proximal end side of the outer peripheral portion of distal end frame 15A and in contact with the bendable tube 80, which is an exterior portion, and a second electrical conductor pattern 17A formed independently of the first electrical conductor pattern 16, having one end that is formed in the through hole 15a and is in contact with the first lens frame 11, and another end that is formed in the channel through hole 15b, including the fifth pattern 17a, the sixth pattern 17b, the seventh pattern 17c, and the eighth pattern 17d, and connected to the second terminal 17e. The second terminal 17e abuts on the metal frame portion 70a inserted into the channel through hole 15b.

In the second embodiment, when static electricity or a leakage current is applied to the distal end frame 15A made of a resin having no electric conductivity, it is possible to conduct electricity from the first lens frame 11 to the ground of the operating unit 7 or the like through the first electrical conductor pattern 16 formed in the distal end frame 15A, that is, the first pattern 16a, the second pattern 16b, the third pattern 16c, and the fourth pattern 16d by an exterior portion such as the first terminal 16e and the bendable tube 80, and it is possible to prevent destruction of the image sensor 20.

In addition, in the second embodiment, the second electrical conductor pattern 17A, which includes the fifth pattern 17a, the sixth pattern 17b, the seventh pattern 17c, and the eighth pattern 17d and is connected to the second terminal 17e, is provided, for confirming a discharge path, independently of the first electrical conductor pattern 16 that performs discharge. As a result, by connecting an electrode of a tester for performing electric conductivity confirmation to the metal frame portion 70a, the electrode can be indirectly connected to the second terminal 17e, and it is possible to easily confirm whether electric conduction is established between the second terminal 17e and the bendable tube 80.

Third Embodiment

Figure 6:
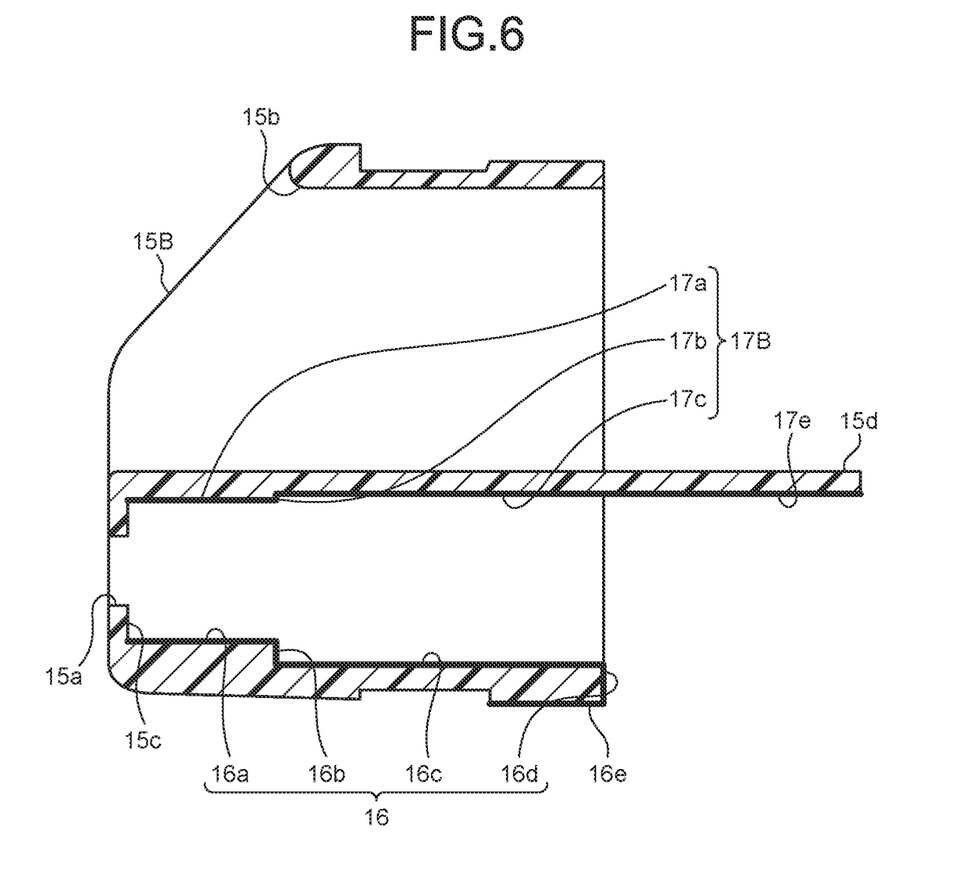
FIG. 6 is a cross-sectional view of a distal end frame according to a third embodiment of the disclosure.
Figure 7:
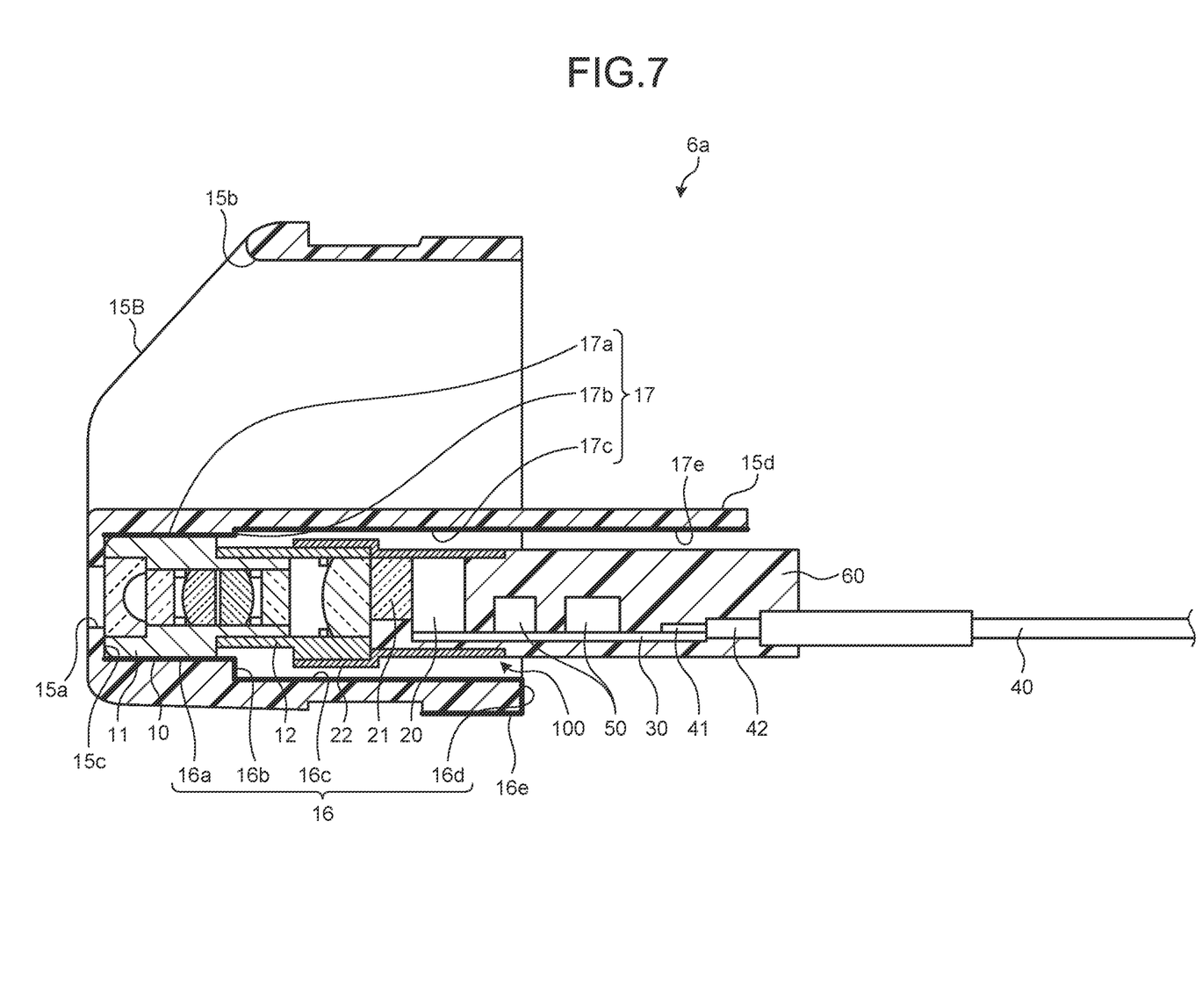
FIG. 7 is a cross-sectional view when an imager is assembled to the distal end frame of FIG. 6.

A distal end frame 15B according to a third embodiment has a protrusion 15d having the second terminal 17e for inspection protruding from the proximal end surface. FIG. 6 is a cross-sectional view of the distal end frame 15B according to the third embodiment of the disclosure. FIG. 7 is a cross-sectional view when the imager 100 is assembled to the distal end frame 15B of FIG. 6.

The distal end frame 15B includes the first electrical conductor pattern 16 having one end that is formed in the through hole 15a through which the imager 100 is inserted and is in contact with the first lens frame 11, and another end that is connected to the first terminal 16e formed on the proximal end side of the outer peripheral portion of distal end frame 15B and in contact with the bendable tube 80, which is an exterior portion, and a second electrical conductor pattern 17B formed independently of the first electrical conductor pattern 16, having one end that is formed in the through hole 15a and is in contact with the first lens frame 11, and another end that is connected to the second terminal 17e of the protrusion 15d, including the fifth pattern 17a, the sixth pattern 17b, and the seventh pattern 17c.

In the third embodiment, when static electricity or a leakage current is applied to the distal end frame 15B made of a resin having no electric conductivity, it is possible to conduct electricity from the first lens frame 11 to the ground of the operating unit 7 or the like through the first electrical conductor pattern 16 formed in the distal end frame 15B, that is, the first pattern 16a, the second pattern 16b, the third pattern 16c, and the fourth pattern 16d by an exterior portion such as the first terminal 16e and the bendable tube 80, and it is possible to prevent destruction of the image sensor 20.

In addition, in the third embodiment, the second electrical conductor pattern 17B, which includes the fifth pattern 17a, the sixth pattern 17b, and the seventh pattern 17c, and is connected to the second terminal 17e, is provided, for confirming a discharge path, independently of the first electrical conductor pattern 16 that performs discharge. Since the second terminal 17e is provided on the protrusion 15d protruding from the proximal end surface of the distal end frame 15B, it is possible to directly connect an electrode of a tester for performing electric conductivity confirmation to the second terminal 17e in a state where the imager 100 is assembled to the distal end frame 15B (state where the bendable tube is not connected), and it is possible to easily confirm whether electric conduction is established between the second terminal 17e and the first terminal 16e. After the electric conduction is confirmed, the protrusion 15d is cut off at the proximal end surface.

Figure 8:
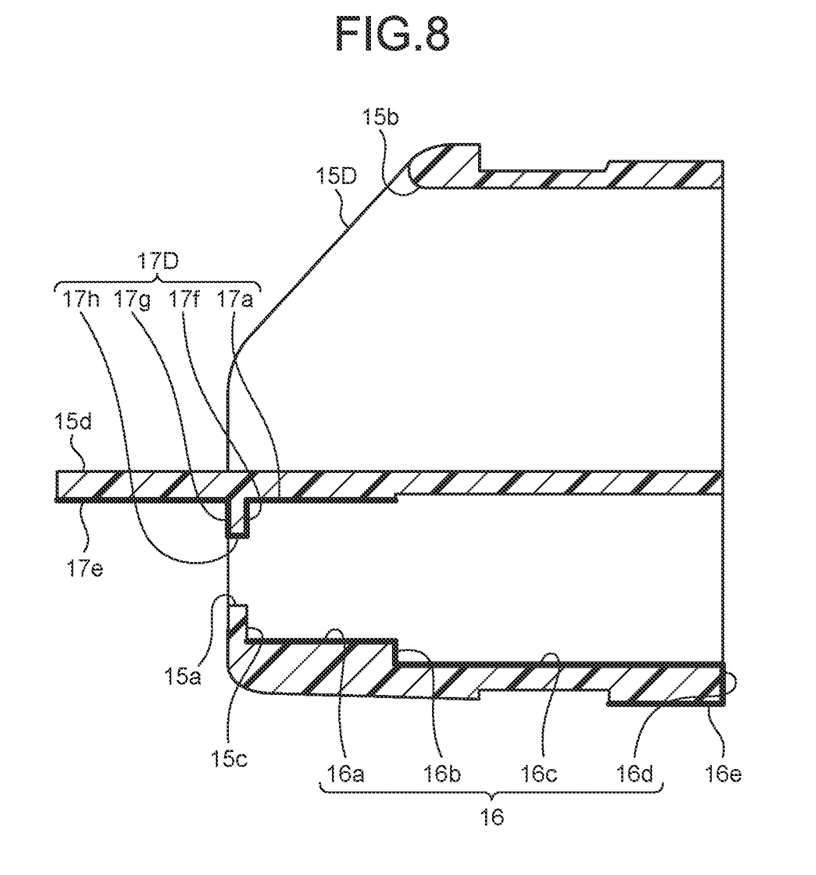
FIG. 8 is a cross-sectional view of a distal end frame according to a modification of the third embodiment of the disclosure.
Figure 9:
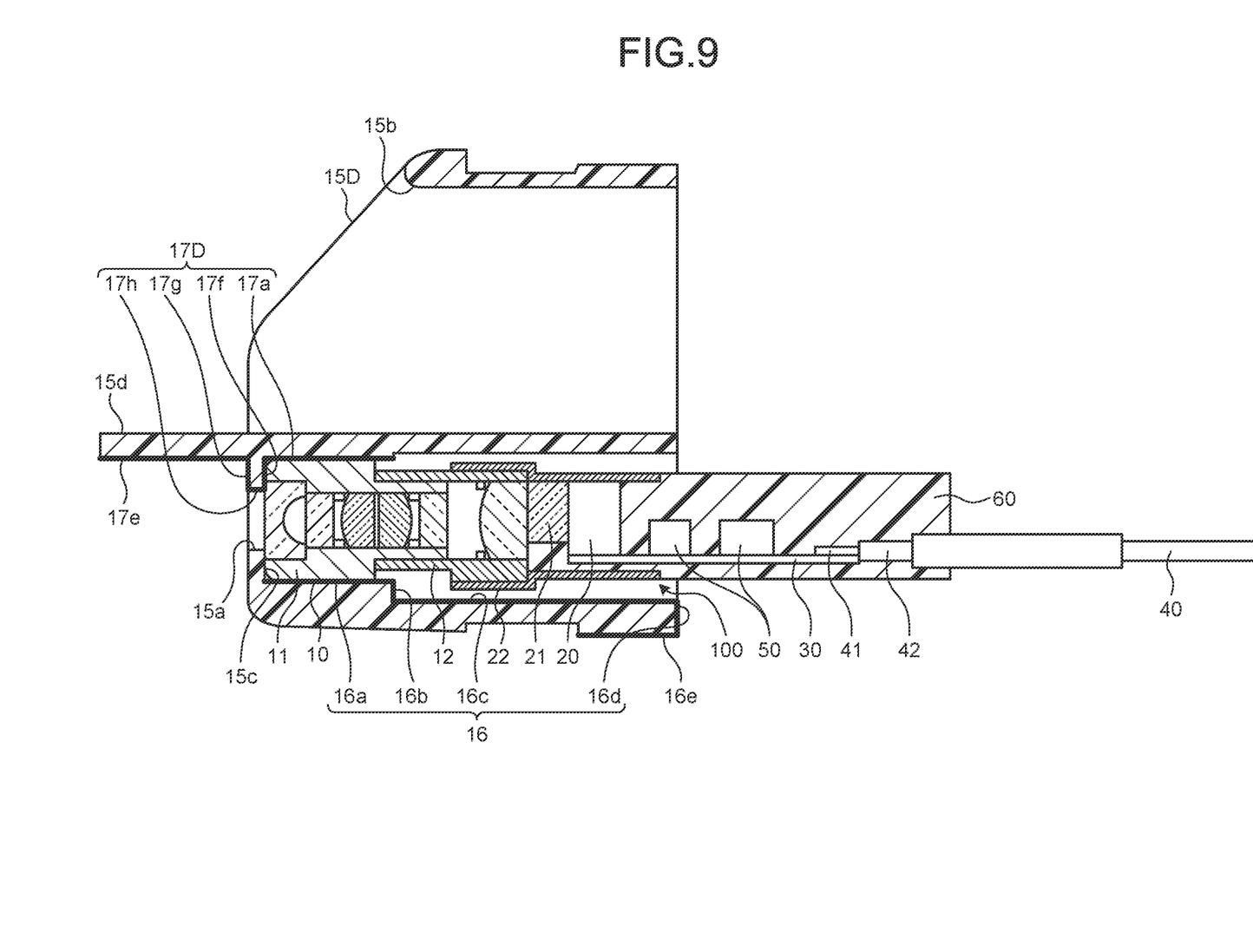
FIG. 9 is a cross-sectional view when the imager is assembled to the distal end frame of FIG. 8.

In the above-described third embodiment, the protrusion 15d is formed on the proximal end surface of the distal end frame 15B, but may be formed on the distal end surface. FIG. 8 is a cross-sectional view of a distal end frame 15D according to a modification of the third embodiment of the disclosure. FIG. 9 is a cross-sectional view when the imager 100 is assembled to the distal end frame 15D of FIG. 8.

The distal end frame 15D includes the first electrical conductor pattern 16 having one end that is formed in the through hole 15a through which the imager 100 is inserted and is in contact with the first lens frame 11, and another end that is connected to the first terminal 16e formed on the proximal end side of the outer peripheral portion of the distal end frame 15D and in contact with the bendable tube 80, which is an exterior portion, and a second electrical conductor pattern 17D formed independently of the first electrical conductor pattern 16, having one end that is formed in the through hole 15a and is in contact with the first lens frame 11 and another end that is connected to the second terminal 17e of the protrusion 15d, including the fifth pattern 17a, a ninth pattern 17f, a tenth pattern 17g, and an eleventh pattern 17h. The ninth pattern 17f, the tenth pattern 17g, and the eleventh pattern 17h are patterns formed on the abutting portion 15c.

In the modification of the third embodiment, when static electricity or a leakage current is applied to the distal end frame 15D made of a resin having no electric conductivity, it is possible to conduct electricity from the first lens frame 11 to the ground of the operating unit 7 or the like through the first electrical conductor pattern 16 formed in the distal end frame 15D, that is, the first pattern 16a, the second pattern 16b, the third pattern 16c, and the fourth pattern 16d by an exterior portion such as the first terminal 16e and the bendable tube 80, and it is possible to prevent destruction of the image sensor 20.

In addition, in the modification of the third embodiment, the second electrical conductor pattern 17D, which includes the fifth pattern 17a, the ninth pattern 17f, the tenth pattern 17g, and the eleventh pattern 17h and is connected to the second terminal 17e, is provided, for confirming a discharge path, independently of the first electrical conductor pattern 16 that performs discharge. Since the second terminal 17e is provided on the protrusion 15d protruding from the distal end surface of the distal end frame 15D, it is possible to directly connect an electrode of a tester for performing electric conductivity confirmation to the second terminal 17e in a state where the imager 100 is assembled to the distal end frame 15D (state where the bendable tube is not connected), and it is possible to easily confirm whether electric conduction is established between the second terminal 17e and the first terminal 16e. After the electric conduction is confirmed, the protrusion 15d is cut off at the proximal end surface.

The distal end portion of the endoscope of the disclosure is useful for an endoscope system that is required to reduce the diameter and the cost.

According to the disclosure, electric conduction of a discharge path can be easily confirmed in a state where the imager is assembled to the distal end frame.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A distal end frame for use with an endoscope, the distal end frame comprising:
    a body comprising an electric insulating material, the body comprising:
        a through hole through which a lens frame is inserted;
        a first electrical conductor pattern comprising:
            a first end disposed on an inner surface of the through hole and formed in contact with the lens frame, and
            a second end connected to a first terminal formed on a proximal end side of an outer peripheral portion of the distal end frame; and
        a second electrical conductor pattern formed independently of the first electrical conductor pattern, the second electrical conductor pattern comprising:
            a third end disposed on the inner surface of the through hole and formed in contact with the lens frame, and
            a fourth end connected to a second terminal.

2. The distal end frame according to claim 1, further comprising a protrusion that includes the second terminal and protrudes from a distal end surface or a proximal end surface of the distal end frame.

3. The distal end frame according to claim 2, wherein the distal end frame is configured to directly or indirectly conduct electricity to the second terminal only when the lens frame is attached to the distal end frame.

4. The distal end frame according to claim 1, wherein the second end of the second electrical conductor pattern is formed in a channel through hole.

5. A distal end portion for use with an endoscope, the distal end portion comprising:
    the distal end frame according to claim 1;
    the lens frame including an objective optical system and an image sensor; and
    an electrically conductive exterior portion having a distal end side connected to a proximal end side of the distal end frame and a proximal end side configured to be connected to a ground of an external device;
    wherein the second end of the first electrical conductor pattern is in contact with the exterior portion,
    the fourth end of the second electrical conductor pattern is not in contact with the exterior portion, and
    the second terminal is configured to directly or indirectly conduct electricity only when the lens frame and the exterior portion are attached to the distal end frame.

6. An endoscope comprising:
    the distal end portion according to claim 5.

7. The distal end portion according to claim 5, wherein the second terminal is provided on the proximal end side of the outer peripheral portion of the distal end frame, and
    the exterior portion having a cut-out exposing the second terminal through the cut out.

8. The distal end portion according to claim 5, further comprising
    a treatment tool channel frame comprising metal, wherein the distal end frame includes a channel through hole through which the treatment tool channel frame is inserted,
    the second terminal is formed in the channel through hole and is in contact with the treatment tool channel frame, and
    the second terminal is configured to conduct electricity through the treatment tool channel frame.

9. The distal end portion according to claim 8, further comprising a resin tube externally fitted to a proximal end side of the treatment tool channel frame.

10. The distal end frame according to claim 1, wherein the first electrical conductor pattern extends proximally from the first end, and
    the second electrical conductor pattern extends proximally from the third end.

11. The distal end frame according to claim 1, wherein the first terminal is disposed distally relative to the second end, and the second terminal is disposed distally relative to the fourth end.

12. An electric conduction confirmation method comprising:
  testing electrical conduction between a first terminal and a second terminal of a distal end frame of an endoscope, wherein the distal end frame comprising:
    a through hole through which a lens frame is inserted,
    a first electrical conductor pattern comprising:
      a first end disposed on an inner surface of the through hole and formed in contact with the lens frame, and
      a second end connected to the first terminal formed on a proximal end side of an outer peripheral portion of the distal end frame, and
    a second electrical conductor pattern formed independently of the first electrical conductor pattern, the second electrical conductor pattern comprising:
      a third end disposed on the inner surface of the through hole and formed in contact with the lens frame, and
      a fourth end connected to the second terminal,
    wherein the testing comprises:
      connecting an electrode of a tester to the second terminal to establish electric conduction between the first terminal and the second terminal; and
      confirming whether electric conduction is established between the first terminal and the second terminal based on the connecting.

13. The electric conduction confirmation method according to claim 12, wherein the second terminal is provided at a protrusion that protrudes from a distal end surface or a proximal end surface of the distal end frame.

14. The electric conduction confirmation method according to claim 13, further comprising cutting off the protrusion at the distal end surface or at the proximal end surface after the confirming whether the electric conduction is established.

15. A distal end portion for use with an endoscope, the distal end portion comprising:
  a lens frame including an objective optical system and an image sensor;
  a distal end frame comprising an electric insulating material and including a through hole through which the lens frame is inserted;
  an electrically conductive exterior portion having a distal end side connected to a proximal end side of the distal end frame and a proximal end side configured to be connected to a ground of an external device; and
  a treatment tool channel frame comprising metal,
  wherein the distal end frame comprising:
    a first electrical conductor pattern comprising:
      a first end being formed in the through hole and in contact with the lens frame, and
      a second end being connected to a first terminal formed on a proximal end side of an outer peripheral portion of the distal end frame and in contact with the exterior portion; and
    a second electrical conductor pattern formed independently of the first electrical conductor pattern, the second electrical conductor pattern comprising:
      a third end being formed in the through hole and in contact with the lens frame, and
      a fourth end being connected to a second terminal formed outside the through hole of the distal end frame and not in contact with the exterior portion, and
    a channel through hole through which the treatment tool channel frame is inserted, and
  the second terminal is formed in the channel through hole and is in contact with the treatment tool channel frame, the second terminal is configured to conduct electricity through the treatment tool channel frame only when the lens frame and the exterior portion are attached to the distal end frame.

16. The distal end portion according to claim 15, wherein the second terminal is provided on the proximal end side of the outer peripheral portion of the distal end frame, and
  the exterior portion having a cut-out exposing the second terminal through the cut-out.

17. The distal end portion according to claim 15, further comprising a protrusion including the second terminal and protruding from a distal end surface or a proximal end surface of the distal end frame.

18. An electric conduction confirmation method comprising:
  testing electrical conduction between a first terminal and a second terminal of a distal end frame of an endoscope, wherein the distal end frame comprising:
    a through hole through which a lens frame is inserted,
    a first electrical conductor pattern comprising:
      a first end formed in the through hole and being in contact with the lens frame, and
      a second end connected to the first terminal formed on a proximal end side of an outer peripheral portion of the distal end frame, and
    a second electrical conductor pattern formed independently of the first electrical conductor pattern, the second electrical conductor pattern comprising:
      a third end formed in the through hole and in contact with the lens frame, and
      a fourth end connected to the second terminal, and
    a channel through hole through which a treatment tool channel frame is inserted, wherein
  the second terminal is formed in the channel through hole and is in contact with the treatment tool channel frame, and
  the second terminal is configured to conduct electricity through the treatment tool channel frame,
  wherein the testing comprises:
    connecting an electrode of a tester to the second terminal to establish electric conduction between the first terminal and the second terminal; and
    confirming whether electric conduction is established between the first terminal and the second terminal based on the connecting.

19. The electric conduction confirmation method according to claim 18, wherein the second terminal is provided at a protrusion that protrudes from a distal end surface or a proximal end surface of the distal end frame.

20. The electric conduction confirmation method according to claim 19, further comprising cutting off the protrusion at the distal end surface or at the proximal end surface after the confirming whether the electric conduction is established.

* * * * *